US00PP15756P3

(12) United States Plant Patent
Miyazaki et al.

(10) Patent No.: US PP15,756 P3
(45) Date of Patent: May 10, 2005

(54) *PETUNIA* PLANT NAMED 'SUNPATIRE'

(50) Latin Name: *Petunia hybrida*
Varietal Denomination: Sunpatire

(75) Inventors: Kiyoshi Miyazaki, Hikone (JP); Kazunari Iwaki, Omihachiman (JP); Takuro Ishihara, Yokaichi (JP)

(73) Assignee: Suntory Flowers Limited, Tokyo (JP)

( * ) Notice: Subject to any disclaimer, the term of this patent is extended or adjusted under 35 U.S.C. 154(b) by 26 days.

(21) Appl. No.: 10/611,359

(22) Filed: Jun. 30, 2003

(65) Prior Publication Data

US 2004/0268457 P1 Dec. 30, 2004

(51) Int. Cl.[7] ..... A01H 5/00
(52) U.S. Cl. ..... Plt./356
(58) Field of Search ..... Plt./356

(56) References Cited

U.S. PATENT DOCUMENTS

PP6,899 P 7/1989 Tsuda et al.
PP6,914 P 7/1989 Tsuda et al.
PP6,915 P 7/1989 Tsuda et al.
PP9,322 P 10/1995 Tachibana et al.
5,523,520 A 6/1996 Hunsperger et al.

FOREIGN PATENT DOCUMENTS

JP 14306 3/2002

OTHER PUBLICATIONS

Catalogue for Profit Organization, 2002 Fall–2003 Spring, No. 78, 5 pages, Published by Sakata Seed Co., Japan, May 2002 with English explanation.

Goldsmith Seeds, 2003–2004 Catalog, 3 pages, Apr. 11, 2003, published by Goldsmith Seeds, Inc., U.S.A.

*Primary Examiner*—Anne Marie Grunberg
*Assistant Examiner*—Annette H Para
(74) *Attorney, Agent, or Firm*—Christie, Parker and Hale, LLP

(57) ABSTRACT

Disclosed herein is a new and distinct variety of *Petunia* plant having a spreading habit. The *Petunia* plant has abundant branching, and great profusion of blooms, the whole plant remaining in bloom for a considerable period of time. The flowers are single and slightly small size, the petals having vivid red color. The bottom color of the corolla throat is moderate red and the outside of the corolla tube is grayish yellowish pink. The plant exhibits high resistance to rain, heat, cold and disease.

2 Drawing Sheets

Botanical/commercial classification: *Petunia hybrida*/*Petunia* Plant.
Varietal denomination: cv. 'Sunpatire'.

BACKGROUND OF THE VARIETY

The present invention relates to a new and distinct variety of *petunia* plant originated from the crossing a seedling called 'Baccarat Red' (♀) (unpatented) and a *Petunia* hybrid variety *Petunia hybrida* Vlim. called 'PF038-1' (♂) unpatented.

The *Petunia* is a very popular plant that is used for flower bedding and potting in the summer season. There are only a few *Petunia* varieties which do not have an upright growth habit and which have a high resistance to rain, heat, and diseases. The *Petunia* plant that we previously filed, i.e. the 'Revolution' series {'Revolution Purple pink' (U.S. Plant Pat. No. 6,915), 'Revolution Brilliant pink' (U.S. Plant Pat. No. 6,914), 'Revolution Brilliant pink-mini' (U.S. Plant Pat. No. 6,899), and 'Revolution Blue vein' (U.S. Plant Pat. No. 9,322)} are decumbent type plants having long stems, a lower plant height, abundant branching, and a high resistance to heat, rain and disease. However, there are only a few *Petunia* varieties having a great profusion of flowers, vivid colored flower petals and a high resistance to rain, heat, cold and diseases. Accordingly, this invention was aimed at obtaining a new variety having vivid red colored petals, many branching and slightly small plant size together with the above features.

The new variety of *petunia* plant according to this invention originated from crossing a seedling called 'Baccarat Red' (♀) and a *Petunia* hybrid variety called 'PF038-1' (♂). The seed of 'Baccarat Red' was bought from Sakata Seed Corp. 'PF038-1' is our *Petunia* breeding line and grown at Yokaichi-shi, Shiga, Japan.

In April 2000, crossing 'Baccarat Red' as female parent and 'PF038-1' as pollen parent was conducted at Yokaichi-shi, Shiga, Japan. In September 2000, 120 seedlings were obtained from that crossing. These seedlings were grown in pots in glasshouses and tested. One new variety was selected in view of their decumbent growth habit and their flower color. That seedling was propagated by cutting from November 2000, and carried out a trial by flower potting and bedding from April 2001, at Yokaichi-shi, Shiga, Japan. The botanical characteristics of that plant were then examined, using similar varieties 'Fantasy Crystal Red' and 'Suncomi' for comparison. As a result, it was concluded that this *petunia* plant is distinguishable from any other variety, whose existence is known to us, and uniform and stable in its characteristics. Then the new variety of *petunia* plant was named 'Sunpatire'.

In the following description, the color-cording is in accordance with the Horticultural Colour Chart of The Royal Horticultural Society, London, England (R.H.S. Colour Chart). A color chart based on The Japan Color Standard for Horticultural Plants (J.H.S. Color Chart) is also added for reference.

The female parent used in the crossing of 'Sunpatire' called 'Baccarat Red' having medium habit while that of the new variety is spreading. The branching is fewer than the new variety. It has medium single flowers and petals having deep reddish orange (near R.H.S. 46A). The bottom color of the corolla throat is dark reddish brown (near R.H.S. 53A) and outside color of the corolla tube is pale purplish pink (near R.H.S. 56B).

The main botanical characteristics of the 'Baccarat Red' are as follows:

Plant:
- *Growth habit.*—Slightly erect.
- *Plant height.*—32 cm.
- *Spreading area of plant.*—Slightly small.
- *Blooming period.*—Early April to late September in the southern Kanto area, Japan.

Stem:
- *Length.*—10 cm.
- *Thickness.*—Main stem 2.8 mm.
- *Pubescence.*—Slightly dense.
- *Branching.*—Medium.
- *Length of internode.*—1.1 cm.
- *Color.*—Moderate olive green (near R.H.S. 146A, J.H.S. 3508).

Leaf:
- *Whole shape.*—Slightly lanceolate. The apex shape is acute, and the base shape is attenuate.
- *Length.*—4.5 cm.
- *Width.*—2.5 cm.
- *Color.*—Upper-side color is moderate olive green (near R.H.S. 146A, J.H.S. 3508). Bottom-side color is moderate yellow green (near R.H.S. 144A, J.H.S. 3513).
- *Pubescence.*—Slightly dense.

Flower:
- *Facing direction.*—Slightly upward.
- *Type.*—Single.
- *Shape of corolla tube.*—Thin.
- *Shape of petal tip.*—Obtuse.
- *Lobation.*—Medium.
- *Undulation of petal margin.*—Slightly weak.
- *Diameter.*—7.5 cm.
- *Color.*—Petal; deep reddish orange (near R.H.S. 46A, J.H.S. 0708). Bottom color of the corolla throat; dark reddish brown (near R.H.S. 53A, J.H.S. 0710). Outside color of the corolla tube; pale purplish pink (near R.H.S. 56B, J.H.S. 9702).
- *Reproductive organs.*—1 normal pistil and 5 normal stamens. Color of pistil is moderate yellow green (near R.H.S. 145C, J.H.S.3310). Color of stamen is pale greenish yellow (near R.H.S. 10D, J.H.S.2903).
- *Peduncle.*—1.5 mm in thickness, and 2.1 cm in.

Physiological and ecological characteristics: Moderate resistance to cold, rain, pests and disease.

The male parent 'PF038-1' used in the crossing of 'Sunpatire' is one of our own *Petunia* breeding line. The *Petunia* plant 'PF038-1' has spreading habit with many branching. It has slightly small single flower, the petals having vivid reddish purple (near R.H.S. 74A). The bottom color of the corolla throat is moderate purple (near R.H.S. 83B) and outside color of the corolla tube is strong purple (near R.H.S. 83D).

The main botanical characteristics of the 'PF038-1' are as follows:

Plant:
- *Growth habit.*—Spreading.
- *Plant height.*—10 cm.
- *Spreading area of plant.*—Medium.
- *Blooming period.*—Early April to late October in the southern Kanto area, Japan.

Stem:
- *Length.*—10 cm
- *Thickness.*—2.0 mm.
- *Pubescence.*—Slightly dense.
- *Branching.*—Many.
- *Length of internode.*—2.0 cm.
- *Color.*—Light yellow green (near R.H.S. 145C, J.H.S. 3503).

Leaf:
- *Whole shape.*—Slightly lanceolate. The apex shape is acute, and the base shape is attenuate.
- *Length.*—5.5 cm.
- *Width.*—3.5 cm.
- *Color.*—Upper-side color is moderate olive green (near R.H.S. 146A, J.H.S. 3508). Bottom-side color is moderate yellow green (near R.H.S. 147B, J.H.S. 3513).
- *Pubescence.*—Normal.

Flower:
- *Facing direction.*—Slightly upward.
- *Type.*—Single.
- *Shape of corolla tube.*—Medium.
- *Shape of petal tip.*—Round.
- *Lobation.*—Medium.
- *Undulation of petal margin.*—Slightly weak.
- *Diameter.*—5.5 cm.
- *Color.*—Petal; vivid reddish purple (near R.H.S. 74A, J.H.S. 9207). Bottom color of the corolla throat; moderate purple (near R.H.S. 83B, J.H.S. 8613). Outside color of the corolla tube; strong purple (near R.H.S. 83D, J.H.S. 8612).
- *Reproductive organs.*—1 normal pistil and 5 normal stamens. Color of pistil is strong yellow green (near R.H.S. 144B, J.H.S.3512). Color of stamen is yellowish white (near R.H.S. 155D, J.H.S.2501).
- *Peduncle.*—1.0 mm in thickness, and 1.7 cm in length.

Physiological and ecological characteristics: Moderate resistance to pest, Strong resistance to cold, rain, heat and diseases.

The main botanical characteristics of similar variety 'Fantasy Crystal Red' used for examination as comparison are as follows:

Plant:
- *Growth habit.*—Erect.
- *Plant height.*—15.5 cm.
- *Spreading area of plant.*—Small.
- *Blooming period.*—Early April to late September in the southern Kanto area, Japan.

Stem:
- *Length.*—9.5 cm.
- *Thickness.*—Main stem 2.8 mm.
- *Pubescence.*—Sparse.
- *Branching.*—Medium.
- *Length of internode.*—2.2 cm.
- *Color.*—Moderate olive green (near R.H.S. 146A, J.H.S. 3508).

Leaf:
*Whole shape.*—Elliptic. The apex shape is acute, and the base shape is attenuate.
*Length.*—3.2 cm.
*Width.*—2.2 cm.
*Color.*—Upper-side color is strong yellow green (near R.H.S.144A, J.H.S.3507). Bottom-side color is moderate yellow green (near R.H.S. 147B, J.H.S. 3513).
*Pubescence.*—Sparse.
Flower:
*Facing direction.*—Slantly upward.
*Type.*—Single.
*Shape of corolla tube.*—Thin.
*Shape of petal tip.*—Obtuse.
*Lobation.*—Medium.
*Undulation of petal margin.*—Weak.
*Diameter.*—4.5 cm.
*Color.*—Petal; vivid red (near R.H.S. 52A, J.H.S.0106) with strong red (near R.H.S. 53B, J.H.S.0415) vein. Bottom color of the corolla throat is dark red (near R.H.S. 183A, J.H.S.0410). Outside color of the corolla tube is moderate red (near R.H.S. 182A, J.H.S.0416).
*Reproductive organs.*—1 normal pistil and 5 normal stamens. Color of pistil is moderate yellow green (near R.H.S. 147D, J.H.S.3511). Color of stamen is light yellow green (near R.H.S. 150D, J.H.S.3303).
*Peduncle.*—1.0 mm in thickness, and 1.0 cm in length.
Physiological and ecological characteristics: Moderate resistance to cold, rain, pest and disease.

The main botanical characteristics of similar variety 'Suncomi' used for examination as comparison are as follows:

Plant:
*Growth habit.*—Decumbent.
*Plant height.*—17 cm.
*Spreading area of plant.*—Large.
*Blooming period.*—Early April to late October in the southern Kanto area, Japan.
Stem:
*Length.*—12 cm.
*Thickness.*—Main stem 1.8 mm.
*Pubescence.*—Normal.
*Branching.*—Many.
*Length of internode.*—1.5 cm.
*Color.*—Light yellow green (near R.H.S. 145C, J.H.S. 3503).
Leaf:
*Whole shape.*—Elliptic. The apex shape is acute, and the base shape is attenuate.
*Length.*—4.5 cm.
*Width.*—2.5 cm.
*Color.*—Upper-side color is moderate yellow green (near R.H.S.146A, J.H.S. 3509). Bottom-side color is moderate yellow green (near R.H.S. 147B, J.H.S. 3513).
*Pubescence.*—Slightly sparse.
Flower:
*Facing direction.*—Slantly upward.
*Type.*—Single.
*Shape of corolla tube.*—Slightly thin.
*Shape of petal tip.*—Round.
*Lobation.*—Shallow.
*Undulation of petal margin.*—Weak.
*Diameter.*—4.5 cm.
*Color.*—Petal; vivid purplish red (near R.H.S. 57C, J.H.S. 9707). Bottom color of the corolla throat; pale yellowish pink (near R.H.S. 37D, J.H.S.1002). Outside color of the corolla tube; light pink (near R.H.S. 49C, J.H.S. 0402).
*Reproductive organs.*—1 normal pistil and 5 normal stamens. Color of pistil is vivid yellow green (near R.H.S. 144B, J.H.S.3506). Color of stamen is yellowish white (near R.H.S. 155D, J.H.S.2501).
*Peduncle.*—1.0 mm in thickness, and 2.0 cm in length.
Physiological and ecological characteristics: Strong resistance to cold, heat, rain and diseases. Moderate resistance to pests.

SUMMARY OF THE VARIETY

The new variety of the *petunia* plant has a spreading growth habit, abundant branching and great profusion blooms with the whole plant remaining in bloom for a considerable period of time. The flowers are single and slightly small size. The petal color is vivid red. The plant has a high resistance to rain, cold, heat and diseases.

BRIEF DESCRIPTION OF THE PHOTOGRAPH

DESCRIPTION OF THE NEW VARIETY

Figure 1:
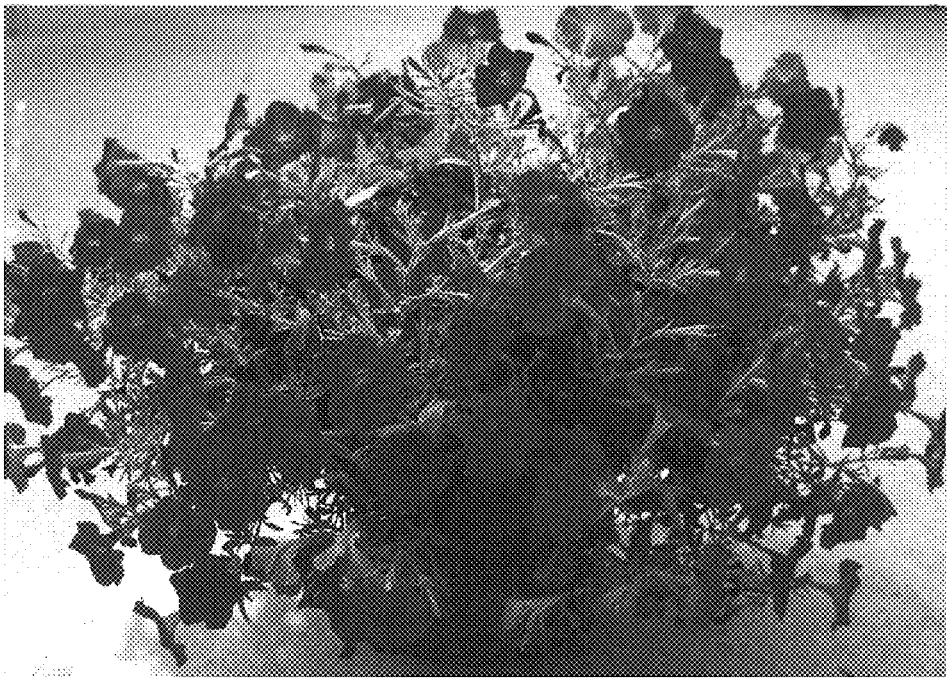
FIG. 1 is a photograph giving a partial view of the new variety of *Petunia* plant named 'Sunpatire' planted in a pot.
Figure 2:
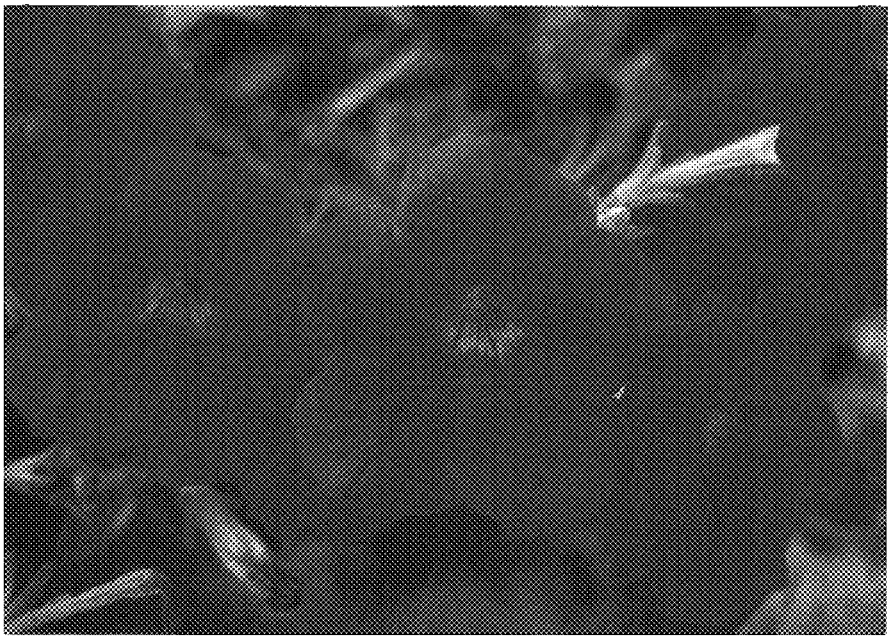
FIG. 2 is a photograph of flowers of the new variety of *Petunia* plant 'Sunpatire'.

The botanical characteristics of the new and distinct variety of *Petunia* plant named 'Sunpatire' grown in Yakaichi-shi, Shiga, Japan (corresponding to U.S. Hardiness Zone 9 ), are as follows.

Plant:
*Growth habit.*—Spreading.
*Plant height.*—33 cm.
*Spreading area of plant.*—Medium.
*Blooming period.*—Early April to late October in the southern Kanto area, Japan. The plant shape does not change throughout this period. A typical flower commonly lasts approximately 5 days on the plant when experiencing a temperature of approximately 20.degree. C.
Stem:
*Length.*—8 cm.
*Thickness.*—1.8 mm.
*Pubescence.*—Normal.
*Branching.*—Many.
*Length of internode.*—4.5 cm.
*Color.*—Moderate olive green (R.H.S. 146A, J.H.S. 3508).
Leaf:
*Whole shape.*—Lanceolate. The apex shape is acute, and the base shape is attenuate.
*Length.*—5.0 cm.
*Width.*—3.2 cm.
*Color.*—Upper side color is moderate olive green (near R.H.S. 146A, J.H.S. 3508). Bottom side color is moderate yellow green (near R.H.S. 144A, J.H.S. 3513).
*Thickness.*—0.9 mm.
*Pubescence.*—Normal.
Flower: Opens horizontally (faces laterally).
*Type.*—Single.

*Shape of corolla tube.*—Approximately 1.0 cm.

*Shape of petal tip.*—Round.

*Length from the throat.*—Approximately 2.5 cm; width approximately 3.0; apex shape — truncate.

*Number of petals.*—5; margin — entire.

*Lobation.*—Shallow.

*Undulation of petal margin.*—Weak.

*Diameter.*—6.0 cm.

*Color.*—Petal; vivid red (near R.H.S. N57A, J.H.S. 0107). Bottom color of the corolla throat; moderate red (near R.H.S. 182A, J.H.S. 0416). Outside color of the corolla tube; grayish yellowish pink (near R.H.S. 186D, J.H.S. 1014).

*Reproductive organs.*—1 normal pistil and 5 normal stamens. Color of pistil is moderate yellow green (near R.H.S. 145C, J.H.S.3310). Color of stamen is pale greenish yellow (near R.H.S. 10D, J.H.S. 2903).

*Petiole.*—Length approximately 3.0 mm, width approximately 1.5 mm, diameter approximately 1.0 mm.

*Sepal.*—Length approximately 1.5 cm, width approximately 2.5 mm; shape is narrowly oblong; apex shape is obtuse; margin is entire.

*Peduncle.*—About 1.5 mm in diameter and about 4.0 cm in length; texture — smooth.

*Hardiness of plant.*—The hardiness of the plant for cold and heat corresponds to USDA Hardiness Zone 9. The plant grows well at temperatures up to 30° C. The lower and upper temperatures for the plant survival has not been evaluated. No serious damage from white fly and aphids has been observed. Fungus and bacterial disease has not been observed.

This new variety of *Petunia* plant is most suitable for flower bedding, potting and large planters. Pinching of old blossoms will enhance the formation of new blossoms.

It is claimed:

1. A new and distinct variety of *Petunia* plant, substantially as herein illustrated and described.

* * * * *